US00RE38074E

(19) United States
(12) Reissued Patent
Recinella et al.

(10) Patent Number: US RE38,074 E
(45) Date of Reissued Patent: Apr. 8, 2003

(54) CONTRAST MEDIUM DELIVERY SYSTEM AND ASSOCIATED METHOD

(75) Inventors: Daniel K. Recinella, Queensbury, NY (US); Eamonn Hobbs, Queensbury, NY (US)

(73) Assignee: AngioDynamics, Inc., Queensbury, NY (US)

(21) Appl. No.: 10/116,486

(22) Filed: Apr. 3, 2002

Related U.S. Patent Documents

Reissue of:
(64) Patent No.: 6,315,762
Issued: Nov. 13, 2001
Appl. No.: 08/966,671
Filed: Nov. 10, 1997

U.S. Applications:
(60) Provisional application No. 60/031,116, filed on Nov. 14, 1996.

(51) Int. Cl.[7] ..... A61M 5/00
(52) U.S. Cl. ..... 604/247; 604/183; 604/535; 604/505
(58) Field of Search ..... 604/523, 533, 604/535, 183, 185, 186, 246, 247, 500, 505, 508

(56) References Cited

U.S. PATENT DOCUMENTS 5,250,034 A * 10/1993 Appling et al. ..... 604/523
5,267,979 A * 12/1993 Appling et al. ..... 604/247
5,569,208 A * 10/1996 Woelpper et al. ..... 604/183
5,575,767 A * 11/1996 Stevens ..... 604/505
5,651,776 A * 7/1997 Appling et al. ..... 604/534

* cited by examiner

*Primary Examiner*—Anhtuan T. Nguyen
*Assistant Examiner*—Michael M Thompson
(74) *Attorney, Agent, or Firm*—Reed Smith

(57) ABSTRACT

A device cooperating with a pump for guiding a contrast medium from a source thereof to a catheter for delivery to a patient's vascular system. The device comprises a dual check valve, a tubular member, an in-line check valve and a three-port stopcock. The dual check valve has an inlet port connectable to the source of contrast medium, an inlet-outlet port connectable to the pump, and an outlet port coupled to the tubular member. The in-line check valve is connected to the tubular member at a point spaced from the dual check valve for preventing fluid flow towards the dual check valve. The stopcock connected at a first port to the in-line check valve, a second port of the stopcock being operatively connectable to the catheter. Using this device, medical personnel infuses contrast medium into the patient from the source without having to disconnect any element from the device during the infusion process.

15 Claims, 2 Drawing Sheets

CONTRAST MEDIUM DELIVERY SYSTEM AND ASSOCIATED METHOD

Matter enclosed in heavy brackets [ ] appears in the original patent but forms no part of this reissue specification; matter printed in italics indicates the additions made by reissue.

CROSS-REFERENCE TO A RELATED APPLICATION

This application relies for priority purposes on U.S. provisional application No. 60/031,116 filed Nov. 14, 1996.

BACKGROUND OF THE INVENTION

This invention relates to a device and a system for delivering contrast medium to a patient. The device and system are especially effective for delivering carbon dioxide gas to the vascular system of a patient. This invention also relates to an associated method for delivering contrast medium such as carbon dioxide gas to a patient.

Delivery systems for contrast media have been used for many years in the medical field. Keeping the system a "closed system" so that no room air will be introduced is critical to the features of these delivery systems. With the advent of carbon dioxide gas or $CO_2$ as a viable fluid for displacing blood in vessels for visualization under Digital Subtraction Angiography (DSA), the need to keep air out of the system is of even greater importance. Air and $CO_2$ are invisible so introduction of air into a $CO_2$ delivery system would pose a danger to a patient if it were inadvertently injected into the vasculature.

$CO_2$ has been shown to be an excellent fluid to be used for displacing blood in vessels. This void that is created in the vessel can be visualized with DSA. But since $CO_2$ is invisible introduction of room air into the system would pose a great danger to the patient. The air would go undetected and, once in the patient's vasculature, could cause a blockage or even an air embolism to the brain resulting in a stroke or death.

Because of this serious safety issue, it would make sense to use a closed system for the safe delivery of $CO_2$. However, the conventional method used for delivering $CO_2$ is connecting a syringe to a $CO_2$ cylinder, filling the syringe with $CO_2$, disconnecting the syringe from the cylinder and re-connecting to a catheter or tube set. If more $CO_2$ is needed, the syringe is disconnected from the catheter and refilled of the cylinder. This method allows for introduction of air into the system at every disconnection.

One method that was developed to reduce the number of disconnections was to attach the $CO_2$ cylinder directly to a stopcock with a syringe attached at on port and the catheter to the patient attached to the other port. When the syringe was to be filled, the stopcock would be opened to the syringe and the cylinder pressure would force $CO_2$ into the syringe. For injection into the patient, the stopcock would be closed to the cylinder and the syringe plunger would be advanced forward pushing the $CO_2$ gas into the catheter and, subsequently, into the patient.

The problem with this method is that the $CO_2$ cylinder pressure is much higher than blood pressure (830 psi vs. 6 psi). If the stopcock is turned the wrong way, the cylinder is open to the catheter and liters of $CO_2$ will be delivered into the patient in less than a minute. Accordingly, the cylinder must be isolated from the patient and the delivery system used must be closed without providing a chance for the introduction of air.

BRIEF DESCRIPTION

It is an object of the invention to provide an improved device or system for delivering contrast medium to a patient's vascular system.

Another object of the present invention is to provide such a device or system wherein air can be effectively eliminated prior to the feeding of the contrast medium to the patient.

It is a further object of the present invention to provide such a device or system wherein highly pressurized sources of contrast medium are isolated from the patient to prevent chance introduction of excessive amounts of contrast medium into the patient.

An additional object of the present invention is to provide such a device or system wherein explosive introduction of gaseous contrast medium (carbon dioxide) into the patient can be minimized or eliminated.

Yet another object of the present invention is to provide such a device or system which is inexpensive and made of essentially off-the-shelf components.

A related object of the present invention is to provide an associated method for infusing contrast medium into a patient's vascular system.

These and other objects of the present invention are attained in a device cooperating with a pump for guiding a contrast medium from a source thereof to a catheter for delivery to a patient's vascular system. The device comprises a dual check valve, a tubular member, an in-line check valve and a three-port stopcock. The dual check valve has an inlet port connectable to the source of contrast medium, an inlet-outlet port connectable to the pump, and an outlet port coupled to the tubular member. The in-line check valve is connected to the tubular member at a point spaced from the dual check valve for preventing fluid flow towards the dual check valve. The stopcock connected at a first port to the in-line check valve, a second port of the stopcock being operatively connectable to the catheter.

Using this device, medical personnel may infuse contrast medium into the patient from the source without having to disconnect any element from the device during the infusion process. The entire system, including the source, the device, the pump and the catheter, is purged of air prior to beginning the infusion and air cannot be reintroduced back into the system during the infusion. The dual check valve permits continued connection of the pump to the system. Thus, where the pump takes the form of a syringe, the pump need not be disconnected from the system between an intake stroke and an ejection stroke of the syringe plunger. The in-line check valve prevents flow of blood from the catheter into the tubular member. It is contemplated that the dual check valve, the syringe and the tubular member are first purged of air by directing contrast medium through those parts of the system and out a third port of the stopcock, and subsequently the catheter, which is connected to the second port of the stopcock, is purged of air by allowing the patient's blood to flow through the catheter and out the third port of the stopcock.

According to another feature of the present invention, the in-line check valve is a dual check valve having an additional inlet port connected to the tubular member, an additional outlet port connected to the stopcock, and an additional inlet-outlet port operatively connectable to an ancillary pump such as a syringe. An additional stopcock may be disposed between the ancillary pump and the additional inlet-outlet port.

This additional structure facilitates a clearing of the catheter of blood prior to infusion of the contrast medium into the patient. The ancillary syringe has a limited volume not significantly greater than the volume in a path extending through the in-line check valve, the stopcock and the catheter. The ancillary syringe is operated to draw contrast medium from the source through the first dual check valve and then to drive the contrast medium through the catheter but not substantially into the patient. The system is now ready for the controlled infusion of contrast medium.

Preferably, the dual check valve, the tubular member, the in-line check valve and the stopcock are all permanently bonded to one another. This prevents the air leakage into the system.

In accordance with another feature of the present invention, the source of contrast medium is a flexible bag. A method for supplying a contrast medium to a patient's vascular system thus comprises operatively connecting the flexible bag to the patient's vascular system via a gas transfer system, purging the gas transfer system of air, and thereafter delivering contrast medium from the flexible bag through the gas transfer system to the patient's vascular system.

The flexible bag contains contrast medium at ambient atmospheric pressure, thus preventing accidental infusion of contrast medium and particularly excessive amounts of contrast medium into the patient. Prior to connecting the flexible bag to the contrast-medium transfer device, the bag is filled multiple times with contrast medium and squeezed empty to clear the bag of air.

In a device or system in accordance with the present invention for delivering contrast medium to a patient's vascular system, air can be effectively eliminated prior to the feeding of the contrast medium to the patient. Highly pressurized sources of contrast medium are isolated from the patient, thereby preventing inadvertent introduction of excessive amounts of contrast medium into the patient. Also, explosive introduction of gaseous contrast medium (carbon dioxide) into the patient can be minimized or eliminated.

DESCRIPTION OF THE PREFERRED EMBODIMENTS

Figure 1:
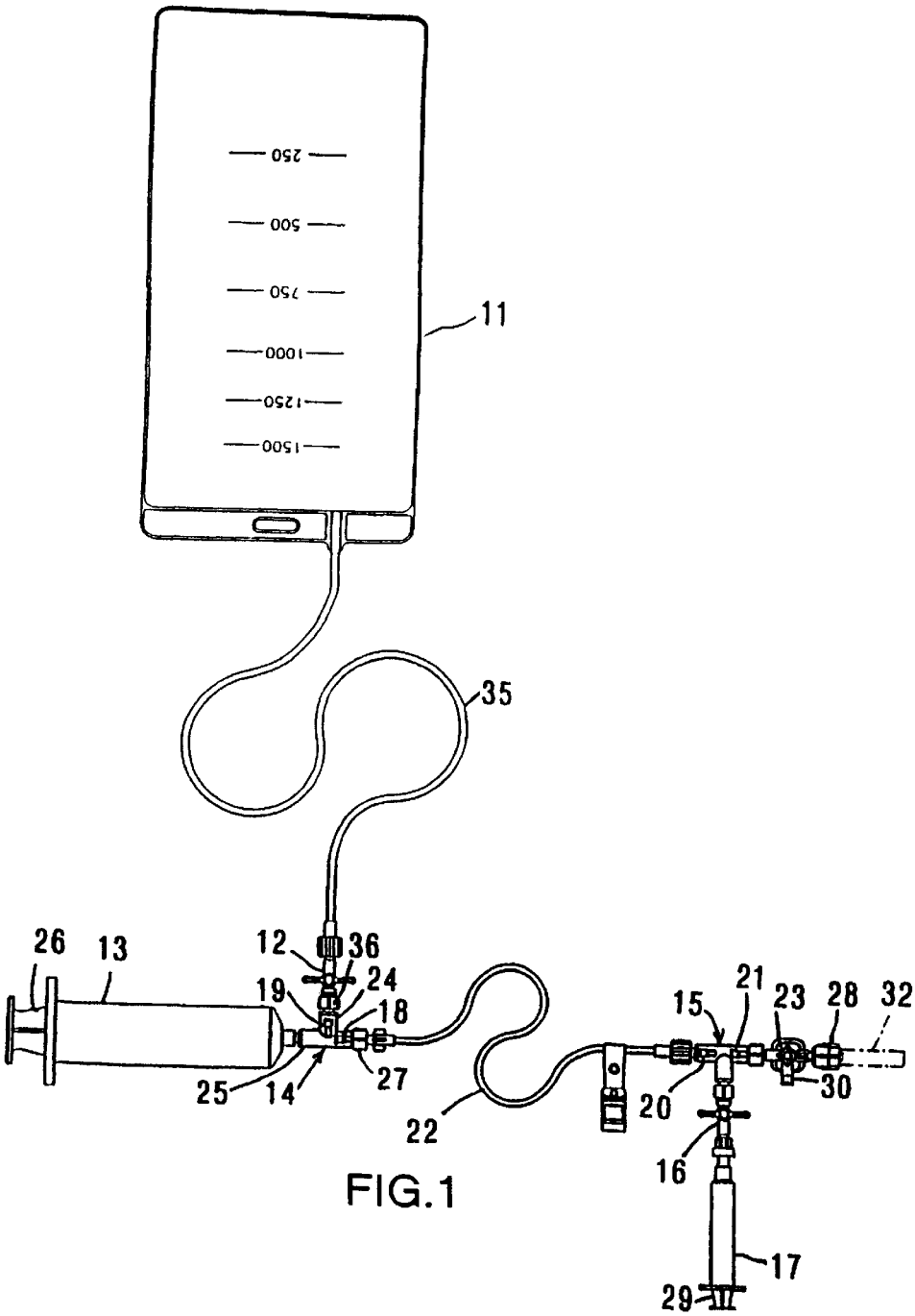
FIG. 1 is a schematic elevational view of a system for controllably infusing carbon dioxide contrast medium into a patient's vascular system, in accordance with the present invention.

As illustrated in FIG. 1, a system for controllably infusing carbon dioxide contrast medium into a patient's vasculature comprises a flexible reservoir bag 11, a one-way reservoir bag stopcock 12, a delivery syringe 13, a dual check valve 14, an in-line check valve 15, a distal one-way stopcock 16, a purge syringe 17, a connecting tube 22, and a patient stopcock 23. This system will remove the high-pressure $CO_2$ cylinder from the vicinity of the patient and maintain a closed system that reduce or eliminate the chance introduction of air into the patient's vasculature.

Reservoir bag 11 is made of a soft elastomeric, non-porous material. When bag 11 is filled to its capacity or just under capacity (500–2000 ml), the bag is at ambient atmospheric pressure. Therefore, bag 11 will not have a tendency to deliver $CO_2$ gas into the patient even if the bag is coupled directly to the patient's vasculature. The patient's blood pressure will be higher than the pressure of the bag. The use of flexible reservoir bag 11 acts as a safety feature for two reasons. First, there is no pressurized source of $CO_2$ gas placed in communication with the patient. Second, bag 11 provides a large reservoir of $CO_2$ so that numerous connections and disconnections are obviated.

Dual check valve 14 is permanently bonded to tube 22. Tube 22 is permanently bonded to in-line check valve 15. In-line check valve 15 is permanently bonded to patient stopcock 23 and distal stopcock 16. Every component in the system except syringes 13 and 17, including dual check valve 14, tube 22, in-line check valve 15, and stopcocks 16 and 23, can withstand pressures from ambient to 1200 psi. Therefore, this system could be used with high pressure injectors, as well as with bag 11.

The system of FIG. 1 is used as follows.

Reservoir bag 11 is coupled to a $CO_2$ cylinder (not illustrated) via a connecting tube 35 and reservoir bag stopcock 12. The cylinder contains 99.7% pure medical grade carbon dioxide and is equipped with a two-stage gas regulator (not shown), a filter (not shown) to remove sub-micron particles, and a Luer-Lok fitting (not shown) to which reservoir bag 11 is coupled. Bag 11 is filled with $CO_2$ gas, disconnected from the cylinder and squeezed until the bag is empty. Bag 11 is then connected to the $CO_2$ cylinder again and re-filled. This process is repeated two to three times to ensure that all the air has been removed from reservoir bag 11. On the last filling, bag 11 is filled and reservoir stopcock 12 is closed. Bag 11 is then detached from the $CO_2$ cylinder and connected to a side or inlet port 24 of dual check valve 14 via a Luer-Lok fitting 36. Inlet port 24 contains a one-way valve 19 which permits fluid to enter the dual check valve 14 through that port but prevents fluid from flowing out of check valve 14. Delivery syringe 13, a Luer-Lok syringe or mechanical injector syringe, is attached to a side or inlet-outlet port 25 of dual check valve 14 and purge syringe 17 is attached to distal stopcock 16.

With all components attached, reservoir stopcock 12 is opened. The plunger 26 of delivery syringe 13 is drawn back, aspirating $CO_2$ gas into the syringe. When plunger 26 is drawn, a one-way valve element 18 in an outlet port 27 of dual check valve 14 closes and does not allow any flow from downstream into the check valve 14. One-way check valve 19 opens and permits fluid flow from reservoir bag 11 into delivery syringe 13.

When plunger 26 of delivery syringe 13 is advanced forward in a pressure stroke, one-way valve element 19 closes and one-way valve element 18 opens, thereby permitting $CO_2$ gas to flow down the tube 22 and out an open port 28 of patient stopcock 13 at the end of the system. By executing this procedure two or three times, the user purges delivery syringe 13, dual check valve 14, tube 22 and in-line check valve 15 of all room air so that only $CO_2$ gas is present in those components of the system.

Purge syringe 17 and distal stopcock 16 are purged next. Upon the opening of distal stopcock 16, purge syringe 17 can draw $CO_2$ gas through check valve 15 and tube 22. A plunger 29 of purge syringe 17 is drawn back. With that action, one-way check valves 18 and 19 of dual check valve 14 and a one-way valve element 20 of in-line check valve 15 are open and allow gas from reservoir bag 11 to flow into purge syringe 17. Another one-way valve element 21 of in-line check valve 15 closes to keep air out of the system. When plunger 29 of purge syringe 17 is depressed in a pressure stroke, the $CO_2$ gas moves forward. One-way valve element 20 closes and one-way valve element 21 opens, thereby permitting $CO_2$ gas to flow out through port 28 at the end of the system. The performance of this action two or three times serves to remove any air contained in in-line check valve 15 and patient stopcock 23.

The above-described priming procedure takes only a few minutes. Once all the air has been removed from the system, a port 28 of patient stopcock 23 is attached to a catheter 32. Blood can be drawn through side port 30 of patient stopcock 23, assuring that all air has been removed from the catheter. When patient stopcock 23 is closed to side port 30, the system is totally closed and room air cannot enter. One-way valve element 21 of dual in-line check valve 15 keeps blood from flowing upstream along tube 22 towards dual check valve 14.

When a $CO_2$ infusion procedure is being performed, it is important to reduce the resistance to gas flow in catheter 32 as much as possible. If the resistance is too high, the gas can build up pressure and exit the catheter explosively. This can result in pain for the patient and inconsistent imaging.

The best way to reduce the resistance is to remove the liquid (saline or blood) that is in catheter 32. This liquid will pose the most significant resistance problems to $CO_2$ flow. To perform a liquid removal procedure, distal stopcock 16 is opened and a limited aliquot (e.g., 3–5 ml) of $CO_2$ is drawn into purge syringe 17. Plunger 29 of purge syringe 17 is subsequently advanced in a pressure stroke. During this pressure stroke, one-way valve element 20 of in-line check valve 15 closes and one-way valve element 21 opens. $CO_2$ gas flows through patient stopcock 23 into catheter 32. This small amount of $CO_2$ displaces the blood or other liquid that is in catheter 32, thereby generating a gas path which is lower in resistance to flow than the patient's blood. One-way valve element 21 of in-line check valve 15 closes from the back pressure of the $CO_2$ gas in catheter 32, thus making it difficult for blood to flow back into catheter 32.

To infuse carbon dioxide into a patient, plunger 26 of delivery syringe 13 is drawn back. One-way check valve element 18 closes and one-way check valve element 19 opens, allowing flow from reservoir bag 11 into delivery syringe 13. Distal stopcock 16 is closed. Plunger 26 of the delivery syringe 13 is advanced in a pressure stroke and the gas is injected into the patient through one-way check valve element 18, tube 22, in-line check valve 15, patient stopcock 23 and catheter 32. For another injection, the retraction and advancing of plunger 26 are repeated. The user can continue until all the $CO_2$ in reservoir bag 11 is used, without having to disconnect any of the elements, e.g., syringe 13, from the system.

Figure 2:
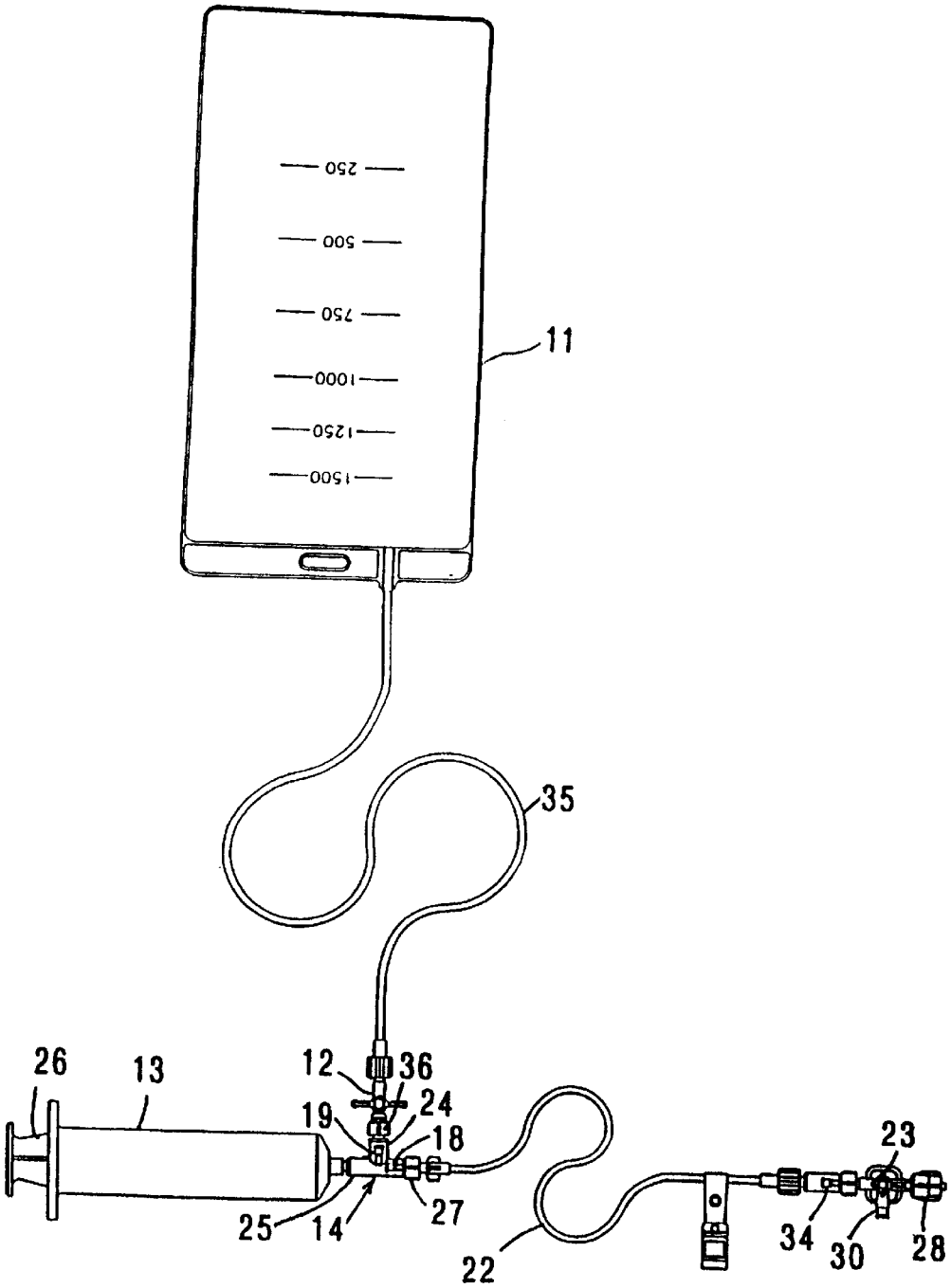
FIG. 2 is a schematic elevational view of a modified system in accordance with the present invention.

FIG. 2 shows a modified design in which in-line check valve 15 has been replaced with an in-line check valve in the form of a single one-way valve 34 and in which stopcock 16 and purge syringe 17 have been removed. The advantage to this design is that there is one less connection so the system becomes even more safe to use. The purge of the liquid from the catheter is done using delivery syringe 13.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A system for delivering contrast medium at low pressure to a catheter for delivery to a patient's vascular system comprising:

a dual check valve adapted to be connected to a lower pressure source of contrast medium, said dual check valve having an inlet port, an outlet port and an inlet-outlet port, said dual check valve containing a first one-way valve at said inlet port automatically responsive to the relatively low pressure at said inlet-outlet port to permit downstream fluid flow and to prevent upstream fluid flow, said dual check valve containing a second one-way valve at said outlet port automatically responsive to the relatively high pressure at said inlet-outlet port to permit downstream fluid flow and to prevent upstream fluid flow, said inlet-outlet port in communication with said first and second one-way valves and adapted to be connected to a pump, a connecting tubular member having an upstream and a downstream end, said upstream end in communication with said outlet port of said dual check valve, suction at said inlet-outlet port by [a] *the* pump causing flow of medium from whatever source is coupled to said inlet port through said first one-way valve into the pump, said second one-way valve preventing fluid flow upstream from said connecting tubular member into the pump, positive pressure at said inlet-outlet port from [a] *the* pump causing fluid flow through said second one-way valve and said outlet port into said tubular member, said first one-way valve preventing upstream fluid flow to [a] *the* source, and a third one-way valve in communication with said downstream end of said tubular member to permit downstream fluid flow from said tubular member and to prevent upstream fluid flow into said tubular member.

2. The system of claim 1 further comprising:

a first stopcock upstream of said inlet port of said dual check valve to turn flow from [a] *the* source on and off.

3. The system of claim 1 further comprising:

a second stopcock downstream of said third one-way valve to turn flow into [a] *the* catheter on and off.

4. The system of claim 2 further comprising:

a second stopcock downstream of said third one-way valve to turn flow into [a] *the* catheter on and off.

5. The system of claim 1 further comprising:

a second dual check valve downstream of said downstream end of said tubular member and incorporating said third one-way valve, said second dual check valve having a second inlet-outlet port adapted to be connected to an ancillary pump, said second dual check valve having a fourth one-way valve in communication with said second inlet-outlet port to permit downstream fluid flow from [an] *the* ancillary pump, said third one-way valve preventing upstream fluid flow from [an] *the* ancillary pump.

6. The system of claim 5 further comprising:

a first stopcock upstream of said inlet port of said dual check valve to turn flow from [a] *the* source on and off.

7. The system of claim 5 further comprising:

a [second] stopcock downstream of said second dual check valve to turn flow into [a] *the* catheter on and off.

8. The system of claim 6 further comprising:

a second stopcock downstream of said second dual check valve to turn flow into [a] *the* catheter on and off.

*9. An apparatus for delivering contrast medium at low pressure to a catheter for delivery to a patient's vascular system comprising:*

*a dual check valve adapted to be connected to a lower pressure source of contrast medium, said dual check valve having a first inlet port, a first outlet port and a first inlet-outlet port,*

*said dual check valve containing a first one-way valve at said first inlet port automatically responsive to the relatively low pressure at said first inlet-outlet port to permit downstream fluid flow and to prevent upstream fluid flow,*

*said dual check valve containing a second one-way valve at said first outlet port automatically responsive to the relatively high pressure at said first inlet-outlet port to permit downstream fluid flow and to prevent upstream fluid flow,*

*said first inlet-outlet port in communication with said first and second one-way valves and adapted to be connected to a pump,*

*a connecting tubular member having an upstream and a downstream end, said upstream end in communication with said first outlet port of said dual check valve,*

*suction at said first inlet-outlet port by the pump causing flow of medium from whatever source is coupled to said first inlet port through said first one-way valve into the pump, said second one-way valve preventing fluid flow upstream from said connecting tubular member into the pump, and*

*positive pressure at said first inlet-outlet port from the pump causing fluid flow through said second one-way valve and said first outlet port into said tubular member, said first one-way valve preventing upstream fluid flow to the source.*

*10. The apparatus of claim 11 further comprising:*

*a first stopcock upstream of said first inlet port of said dual check valve to turn flow from the source on and off.*

*11. The apparatus of claim 10 further comprising:*

*a second stopcock on said downstream end of said tubular member to turn flow into the catheter on and off.*

*12. The apparatus of claim 9 further comprising:*

*a stopcock on said downstream end of said tubular member to turn flow into the catheter on and off.*

*13. The apparatus of claim 9 further comprising:*

*an in-line check valve connected to said downstream end of said tubular member, wherein said in-line check valve has a second inlet port in which said tubular member is connected, a second inlet-outlet port adapted to be connected to an ancillary pump, and a second outlet port connected to a first stopcock which is connected to the catheter.*

*14. The apparatus of claim 13 further comprising:*

*a second stopcock upstream of said first inlet port of said dual check valve to turn flow from the source on and off.*

*15. The apparatus of claim 14 further comprising:*

*a third stopcock disposed between the ancillary pump and the second inlet-outlet port downstream said in-line check valve to turn flow into the catheter on and off.*

* * * * *